Figure 1:
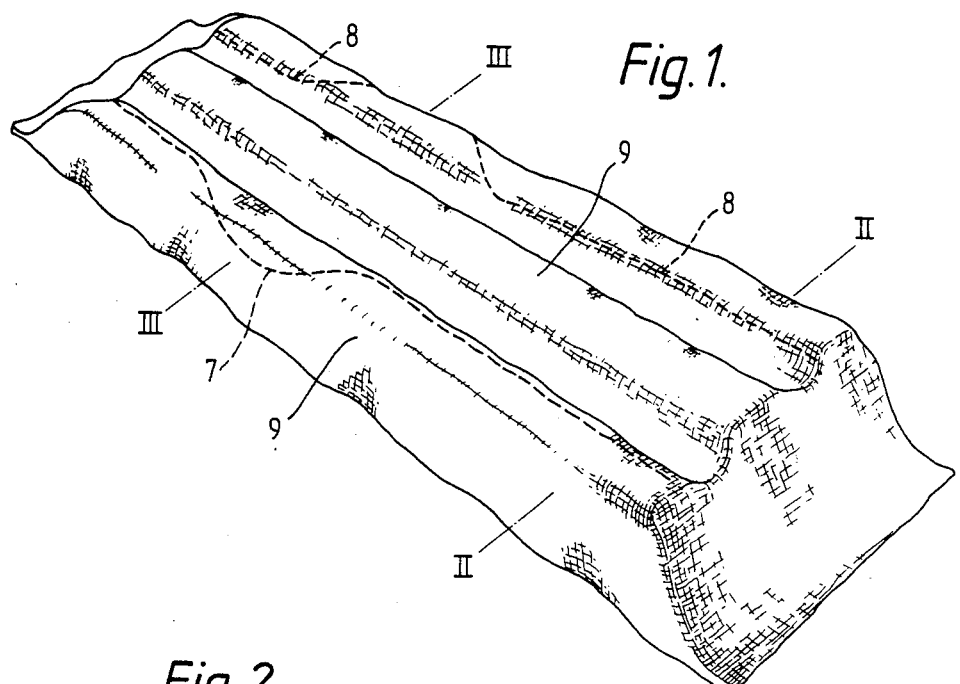

United States Patent [19]

Cottenden et al.

[11] Patent Number: 4,753,644
[45] Date of Patent: Jun. 28, 1988

[54] INCONTINENCE PADS

[75] Inventors: Alan M. Cottenden, Bedford; John Morgon, Lancing, both of England

[73] Assignee: National Research Development Corporation, London, England

[21] Appl. No.: 58,602

[22] Filed: Jun. 4, 1987

Related U.S. Application Data

[63] Continuation of Ser. No. 914,580, Oct. 3, 1986, abandoned, which is a continuation of Ser. No. 600,290, Apr. 13, 1984, abandoned.

[30] Foreign Application Priority Data

Apr. 19, 1983 [GB] United Kingdom ............... 83 10581
Jan. 31, 1984 [GB] United Kingdom ............... 84 02507

[51] Int. Cl.[4] ............................................. A61F 13/16
[52] U.S. Cl. ..................................................... 604/378
[58] Field of Search ................... 604/369, 378, 385.1, 604/370

[56] References Cited

U.S. PATENT DOCUMENTS

| | | | |
|---|---|---|---|
| 3,375,827 | 4/1968 | Bletzinger | 604/369 |
| 3,572,342 | 3/1971 | Lindquist et al. | 604/369 |
| 3,575,174 | 4/1971 | Mogor . | |
| 3,699,966 | 10/1972 | Chapuis | 604/378 |
| 3,741,212 | 6/1973 | Schutte | 604/378 |
| 3,771,525 | 11/1973 | Chapuis . | |
| 3,901,240 | 8/1975 | Hoey | 604/369 |
| 3,916,900 | 11/1975 | Breyer et al. | 604/369 |
| 3,999,549 | 12/1976 | Poncy et al. | 604/369 |
| 4,029,100 | 6/1977 | Karami | 604/369 |
| 4,029,101 | 6/1977 | Cheskq et al. | 604/378 |
| 4,040,423 | 8/1977 | Jones, Sr. | 604/378 |
| 4,410,324 | 10/1983 | Sabee | 604/385 A |
| 4,490,147 | 12/1984 | Pierce et al. | 604/378 |

FOREIGN PATENT DOCUMENTS

| | | |
|---|---|---|
| 0108637 | 5/1984 | European Pat. Off. . |
| 2008938 | 1/1970 | France . |
| 2119193 | 8/1972 | France . |
| 169087 | 9/1921 | United Kingdom . |
| 2148126B | 7/1987 | United Kingdom . |

Primary Examiner—John D. Yasko
Attorney, Agent, or Firm—Stevens, Davis, Miller & Mosher

[57] ABSTRACT

An incontinence device consisting of a rectangular pad of absorbent material incorporating along its upper surface at least one strip of a skeleton polyester foam material, the function of which is to enable urine to flow rapidly to the surface of those regions of the pad not immediately saturated by urine. In a preferred embodiment there are provided three strips of skeleton foam, two peripheral and one along the center line of the pad, to enhance further the capability of the device to absorb urine at high flow rates. A layer of hydrophyllic material may be provided between the foam strips and an outer permeable cover to enhance the wetting properties of the device at low flow rates and to eliminate discomfort caused to the patient by the rough surface of the foam material.

10 Claims, 2 Drawing Sheets

INCONTINENCE PADS

This application is a continuation of application Ser. No. 914,580, filed Oct. 3, 1986, now abandoned, which in turn is a continuation of application Ser. No. 600,280, filed Apr. 13, 1984, now abandoned.

This invention relates to incontinence pads, in particular those suitable for infants or incontinent patients for whom the rate of urine flow might be high.

Absorbent pads are commonly, although not exclusively, used by women. There are many of these products on the market, each using an absorbent core of cotton wool, cellulose wadding and/or woodflock encased in a permeable envelope which often has a waterproof backing. Pants of polythene or some other waterproof material are sometimes used in conjuction with the pads. The largest of these pads is capable of absorbing about 300 cc of urine without leaking, provided the flow rate from the urethra is low. Otherwise, the pad becomes saturated locally and lateral leakage occurs as the absorbent materials used are incapable of distributing urine rapidly to the boundaries of the pad.

Attempts have been made to overcome this problem by interposing between the surface of the pad to be worn against the skin (hereinafter called the upper surface of the pad) and the absorbing and retaining layer of material within the pad a second layer of absorbent material through which urine may pass more freely so that the amount of likelihood of leakage is reduced. In UK Pat. No. 1404453, for example, a fabric formed of cotton yarn and in UK Pat. No. 978,084 a layer of cotton wool fibres serve this purpose. UK Pat. No. 1581162 discloses a pad having a blend of absorbent and nonabsorbent materials whose purpose is to separate the main absorbent layer from the upper surface so that the upper surface stays dry for a longer period.

None of these materials or arrangements provides a pad having the property of dispersing urine readily to the entire layer of absorbent material at any reasonably required rate; this however is a highly desirable feature if it can be provided at low cost.

This invention consists of an elongate pad containing absorbent material retained within a water-pervious cover, the pad incorporating at least one strip of transmitting material having substantially no resistance to liquid flow, the strip extending longitudinally on the upper surface of the pad and being located to provide a passage along which urine not immediately absorbed by the absorbent material can flow to a part of the pad not saturated and thus able to absorb urine.

In one embodiment of the invention one strip extends centrally and longitudinally between the absorbent material and the cover. Such an arrangement may however advantageously incorporate additional longitudinal strips of transmitting material one located close to each long edge of the pad. Such additional peripheral strips may be located below the cover (ie in contact with the absorbent material) but in an alternative embodiment the strips are attached above the cover; it has been found that in some cases such an arrangement may assist in reducing the lateral leakage of urine.

The pad may in addition incorporate an impervious cover over its lower surface, which cover may incorporate means for retaining the pad against the patient. In this case, the two peripheral strips of the previous embodiment may be replaced by a single layer of transmitting material located between the absorbent material and the impervious cover and extending over the entire lower surface and sides of the pad and also over both peripheral parts of the upper surface. This latter form of the invention may be reproduced by the insertion by the patient of an absorbent pad consisting simply of absorbent material within a pervious cover into an adapted elongate receptacle whose shape conforms to the lower surface, edges and upper peripheral surface of the pad, the receptacle being formed by an outer layer of impervious material lined throughout or within its side and upper walls with a layer of the said transmitting material.

It may be preferable in some applications for the absorbent pad, which can be undesirably bulky even when dry, to be replaced by an equivalent, but more compact, appliance containing a hydrogel or similar hydrophyllic substance.

The transmitting material may take the form of a polyester open cell foam, for example of the type used commercially for its acoustical transparency or as a filter. Such a material is sufficiently resilient to maintain a fluid passage adjacent to the absorbent material except on the application of direct pressure, and its pore size can be chosen so as not to be so small to permit meniscus formation and not to be so large to cause difficulty in covering and discomfort to the patient. Materials having 10 or 20 pores per inch have been found suitable for the purpose.

One characteristic of this type of transmitting material is that the loose ends of the cell walls left by the cutting process can form "spikes" on the surface which cause discomfort. This discomfort can be eliminated by subjecting the particular surface before use to sufficient heat to soften a thin layer of material—this can be done without destroying the resistance of the material as a whole—or a layer of paper tissue may be interposed between the cover and the transmitting material.

However, this problem may be overcome by interposing a layer of material such as cotton wool between the cover and the transmitting material. The interposing of such a hydrophyllic material also overcomes another problem—that although the device is highly effective in coping with high flow rates of urine the transmitting material is not wetted by urine. The urine is therefore not readily absorbed at low flow rates through that part of the permeable cover in contact with the foam and at these rates the urine would tend to enter the device only through that part of the cover directly in contact with the absorbent pad.

Figure 2:
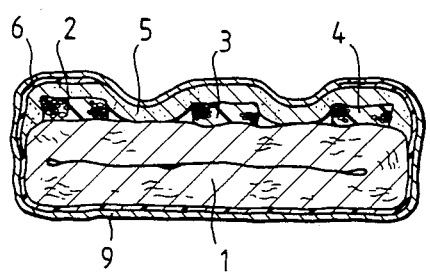
Figure 3:
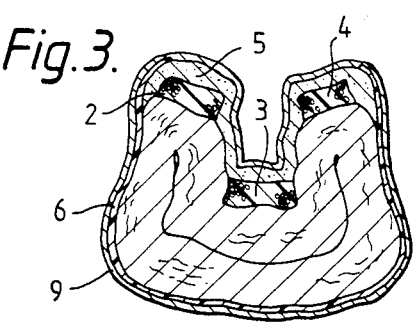
Figure 4:
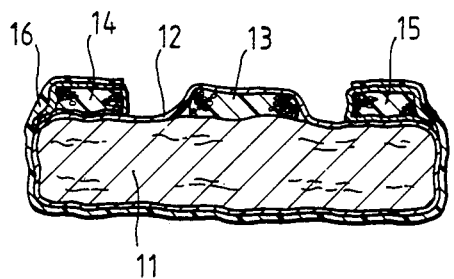
Figure 5:
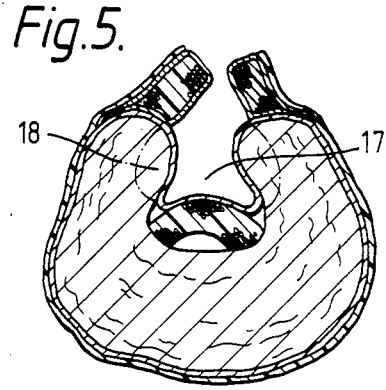
Figure 6:
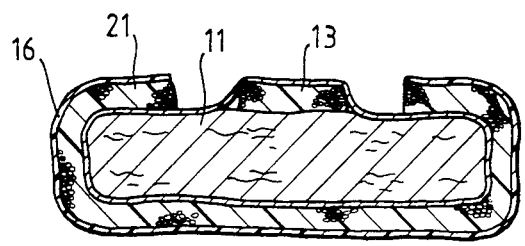
Figure 7:
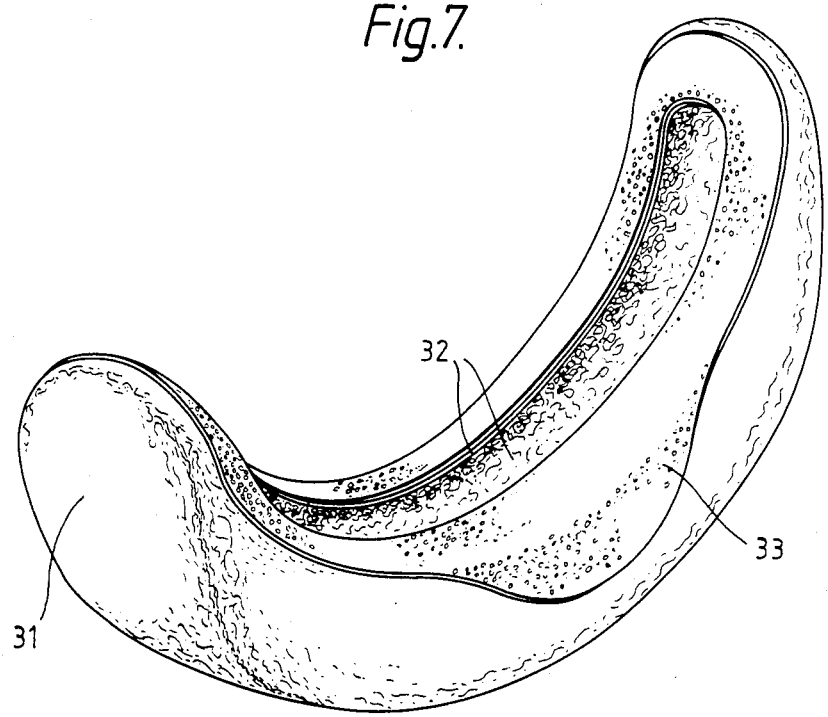

By way of example, embodiments of the invention will now be described with reference to the accompanying drawings of which FIG. 1 is a plan view of a device incorporating three transmitting strips in accordance with the invention FIG. 2 is a section along the lines II—II of FIG. 1, FIG. 3 is a similar section illustrating how the shape of the device is modified in use, as a result of compression by the particat's legs, FIGS. 4 and 5 are similar sections of an alternative embodiment of the invention, FIG. 6 is a similar section of a device in which the peripheral strips of the embodiment illustrated in FIGS. 4 and 5 have been replaced by a single layer of material, and FIG. 7 is a perspective view of a washable receptacle for an absorbent pad.

With reference to FIGS. 1 to 3, an incontinence pad consists of an absorbent layer of woodflock 1 on the uper surface (when in use) of which are located 3 strips of skeleton polyester foam 2, 3 and 4 each having a thickness of 0.2 inch and a mesh of 10 pores per inch. One strip is located along the centre line of the pad and the other two are along the peripheral edges. A layer of cotton wool 5 extends over the entire upper surface of the woodflock and strips of foam, and the woodflock, foam and cotton wool are in turn covered by an impervious plastic backing 6 which however does not cover the centre portion of the upper surface of the pad or those regions of the upper surface to be worn between the legs. The extent of the plastic backing is indicated by the lines 7, 8 of FIG. 1 (the padding would not normally be visible). The whole assembly is enclosed within a water-pervious cover stock 9.

In the embodiment illustrated in FIGS. 4 and 5, a rectangular pad 11 consisting of woodflock and paper is encased in a pervious bonded rayon envelope 12. Three strips of skeleton polyester foam 13, 14 and 15 extend along the top surface of the pad 11. One strip 13 is located along the centre line of the pad and inside the envelope 12, and the other two strips lie close to the long edges of the pad and are located outside the envelope 12. The latter two strips are retained in position by firstly wrapping them in a thin sheet of bonded rayon and then glueing the two free edges of the rayon sheet together and to one edge of the pad. After assembly, the two ends of the envelope 12 are folded over and glued in place to retain further the pad and strips. A thin, impervious, plastic backing 16 is then applied across the top surface of the peripheral strips 14 and 15 and the edge and bottom face of the pad 11.

It can be seen that in use, when the device becomes compressed, particularly between the legs where the section of FIG. 4 is modified to resemble FIG. 5, the backing 16 forms a barrier to the lateral flow of urine voided into the space 17: urine will initially be absorbed readily by the pad 11 but as the surface region 18 becomes saturated the maximum rate of absorption is greatly reduced. Whenever the rate of urine flow exceeds the absorption rate the excess can however flow readily along the strips 13, 14 and 15 to other parts of the pad which are not yet saturated.

In FIG. 6, the strips 14 and 15 have been replaced by a single layer of skeleton polyester foam 21 extending across the entire inner surface of the impervious backing 16. Its performance in use is similar to the embodiment just described: the layer 21 permits the flow of urine to the underside of the pad and the effective absorbing surface of the pad 11 is therefore increased.

FIG. 7 illustrates a washable receptacle into which a disposable pad, either of conventional form or a pad similar to one described above, but without the peripheral strips, may be placed. The receptacle consists of an outer casing 31 of a flexible, impervious, plastics material shaped to fit snugly over the type of pad to be used. A layer 32 of skelton polyester foam having 10 pores per inch is bonded to the inner surface of the outer casing 31 to act as a transmitting layer, and for patient comfort the top surface and the central portion of the long sides of the outer casing 31 are covered in a soft, very fine (60 pores per inch) foam material 33. In use, a pad is retained within the closed ends of the receptacle, and excess urine flow passes across the lower surface of the pad through the layer 32.

Variants of the above, within the scope of the invention, will be readily apparent to those skilled in the art.

Thus, for example, the strips of transmitting material may by a number of arrangements be located partly between the pad and the envelope and partly to form a layer entirely within the pad. By this means, the flow of urine can be enhanced through the thickness of the pad as well as across its surface.

The transmitting material itself may not necessarily be a polyester; it may be preferably biodergradable so that disposal presents fewer problems.

We claim:

1. An incontinence device comprising an elongate water-pervious cover, a pad consisting of absorbent material contained within said cover, and at least one strip of transmitting material extending longitudinally on the upper surface of said pad to cover the portions of said upper surface adjacent to both long edges of the pad, the transmitting material being hydrophobic having a three-dimensional opencelled structure defining pores of non-capillary size to offer substantially no resistance to liquid flow in any direction therethrough so that said strip provides a passage along which urine, not immediately absorbed by said pad, can flow readily to the surface of an unsaturated part of the pad.

2. An incontinence device according to claim 1 having two of said strips of transmitting material, located on the upper surface of said pad adjacent to the long edges of the pad respectively.

3. An incontinence device according to claim 1 including a layer of hydrophyllic material interposed between the said transmitting material and said water-pervious cover.

4. An incontinence device according to claim 1 incorporating an additional strip of transmitting material located centrally along and in contact with the upper surface of said pad.

5. An incontinence device according to claim 1 incorporating a water-impervious layer which covers the lower surface and long edges of the device and the outer surface of the strips which cover the lateral portions of the upper surface of said pad.

6. An incontinence device according to claim 1 in which said strip of transmitting material extends over the lower surface, long edges and both lateral portions of the upper surface of said pad, the outer surface of said strip incorporating a layer of water-impervious material.

7. An incontinence device according to claim 1 in the form of a pocket in which:
   the extent of said pocket is such as to surround said pad completely except for an aperture on one face through which urine may be received by said pad;
   the transmitting material is affixed to and forms an internal lining of said pocket;
   said pad is replaceably insertable into said pocket; and
   the outer surface of said pocket includes a water-impervious layer.

8. An incontinence device according to claims 5, 6, or 7 in which said outer impervious layer consists of latex.

9. An incontinence device according to claim 1 in which those areas of the device which may come into contact with the wearer are covered with a soft foam material.

10. An incontinence device according to claim 1 in which said transmitting material is a polyester open cell foam having a pore size of between 10 and 20 pores per inch.

* * * * *